United States Patent [19]

Choi

[11] Patent Number: 5,602,107
[45] Date of Patent: Feb. 11, 1997

[54] POUR-ON FORMULATIONS CONSISTING OF GYLCOLS, GLYCERIDES AND AVERMECTIN COMPOUNDS

[75] Inventor: Hoo-Kyun Choi, Blue Bell, Pa.

[73] Assignee: Merck & Co., Inc., Rahway, N.J.

[21] Appl. No.: 561,208

[22] Filed: Nov. 20, 1995

Related U.S. Application Data

[63] Continuation of Ser. No. 333,937, Nov. 3, 1994, abandoned, which is a continuation of Ser. No. 59,787, May 10, 1993, abandoned.

[51] Int. Cl.⁶ .................. A61K 31/70; A61K 31/225; A61K 31/045
[52] U.S. Cl. .................. 514/30; 514/547; 514/724; 514/947
[58] Field of Search ................ 514/30, 547, 724, 514/947

[56] References Cited

U.S. PATENT DOCUMENTS

| | | | |
|---|---|---|---|
| 3,950,360 | 4/1979 | Aoki et al. | 549/30 |
| 4,173,571 | 11/1979 | Chabala et al. | 549/264 |
| 4,199,569 | 4/1980 | Chabala et al. | 514/30 |
| 4,310,519 | 1/1982 | Albers-Schonberg et al. | 514/30 |
| 4,916,120 | 4/1990 | Röben et al. | 514/30 |

FOREIGN PATENT DOCUMENTS

| | | |
|---|---|---|
| 0045655A3 | 2/1982 | European Pat. Off. . |
| 0051786A1 | 5/1982 | European Pat. Off. . |
| 0120286A1 | 10/1984 | European Pat. Off. . |
| 0137627A3 | 4/1985 | European Pat. Off. . |
| 0146414A3 | 6/1985 | European Pat. Off. . |
| 0193347A3 | 9/1986 | European Pat. Off. . |
| 0249409A3 | 12/1987 | European Pat. Off. . |
| 0329460A2 | 8/1989 | European Pat. Off. . |
| 0432494A2 | 6/1991 | European Pat. Off. . |
| 2599220 | 12/1987 | France . |

*Primary Examiner*—Kevin E. Weddington
*Attorney, Agent, or Firm*—Sylvia A. Ayler; Mark R. Daniel

[57] ABSTRACT

There is disclosed a topical pour-on formulation containing glycols, glycerides, or their derivatives and an avermectin compound (active ingredient) which has been discovered to provide superior efficacy against endoparasites and ectoparasites when compared to conventional formulations and to maintain the concentration of the active compound in the milk of dairy animals below a safe concentration for human consumption. The formulation contains the avermectin active ingredient and at least 50% of the glycol or glyceride.

9 Claims, No Drawings

POUR-ON FORMULATIONS CONSISTING OF GYLCOLS, GLYCERIDES AND AVERMECTIN COMPOUNDS

This is a continuation of application Ser. No. 08/333,937 filed on Nov 3, 1994 which is now abandoned which is a continuation of application Ser. No. 08/059,787 filed on May 10, 1993, now abandoned.

BACKGROUND OF THE INVENTION

The avermectin series of compounds are potent anthelmintic and antiparasitic agents against internal and external parasites. The natural product avermectins are disclosed in U.S. Pat. No. 4,310,519 to Albers-Schonberg et al., and the 22,23-dihydroavermectin compounds are disclosed in Chabala et al., U.S. Pat. No. 4,199,569. Administration of the avermectin compounds occur orally, parenterally or topically.

However, the conventional topical formulations do not provide acceptable efficacy against ectoparasites, especially against Chorioptes. Often times these formulations fail due to the lack of extended efficacy. Additionally, conventional formulations of current medicinal agents require a withdrawal period of a few weeks after application of the active compound before any milk can be withdrawn from dairy animals for human consumption.

SUMMARY OF THE INVENTION

This invention is concerned with avermectin topical pour-on formulations which effectively eliminate both ectoparasites, especially Chorioptes, and endoparasites of animals such as cattle, swine, etc., and which unexpectedly provides a zero milk withdrawal time for topically applied antiparasitic agents with regard to dairy animals. The formulations are prepared using propylene glycol esters, glycerides, or their derivatives as the carrier. Thus, it is an object of this invention to describe such ectoparasitic and endoparasitic efficacy. Another object is to describe the avermectin compounds which may be employed in the formulation. A still further object is to describe how the concentration of the active compound in the milk of dairy animals is maintained below a concentration level that provides for a zero withdrawal period for human consumption. Additional objects will become apparent after a reading of the following description.

DESCRIPTION OF THE INVENTION

This invention consists of a topical pour-on formulation of a gylceride, glycol, or a derivative thereof as a carrier and an avermectin compound which has been found to effectively eliminate both ectoparasites, especially Chorioptes, and endoparasites, while simultaneously maintaining the concentration of the active compound in the milk of dairy animals below an adequate concentration period for human consumption to provide a zero milk withdrawal time for topically applied endectocides [milk concentration of 4"-acetylamino-4"-deoxyavermectin B1 (4"-aa-4"deoxy) for zero mil withdrawal is 48 ng/ml].

The carriers are oleyl alcohol, propylene glycol and its esters such as propylene dicaprylate/dicaprate, propylene glycol laurate, and the like, glycol ethers such as diethylene glycol monoethyl ether, diethylene glycol monobutyl ether, diethylene glycol diethyl ether and the like, and glycerides such as PEG-6 caprylic/capric triglyceride, caprylic/capric diglyceryl succinate, polyglycolysed glycerides, and the like, preferably propylene caprylate/caprate or caprylate caprate glyceride, and is available under such brand names as Miglyol 810, 812, 818, 829 and 840, Softigen and Labrasol®. The (/) in propylene dicaprylate/dicaprate and PEG-6 caprylic/capric triglycerides indicates a mixture of the two components in a ratio of 65–80/15–30.

The above carriers imparts to the formulation good penetration and spreadability of the active compound even at cold temperatures.

The avermectin compounds preferred for use in this formulation have the following general structure:

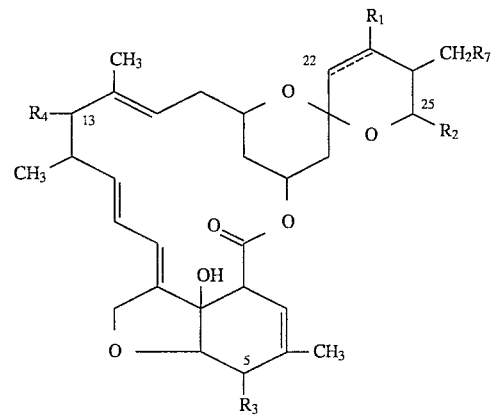

where the broken line indicates a single or a double bond at the 22,23-positions;

$R_1$ is hydrogen or hydroxy provided that $R_1$ is present only when the broken line indicates a single bond;

$R_2$ is alkyl of from 1 to 6 carbon atoms or alkenyl of from 3 to 6 carbon atoms or cycloalkyl of from 3 to 8 carbon atoms;

$R_3$ is hydroxy, methoxy or $=NOR_5$, where $R_5$ is hydrogen or lower alkyl;

$R_7$ is hydrogen, hydroxy, or lower alkyl; and $R_4$ is hydrogen, hydroxy, poly C(1–6) alkoxy or

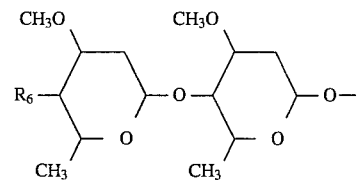

where $R_6$ is hydroxy, amino, mono-or di-$C_1$ to $C_6$ alkylamino or $C_1$ to $C_6$ alkanoylamino.

The preferred compounds of the instant invention have the following structural formula:

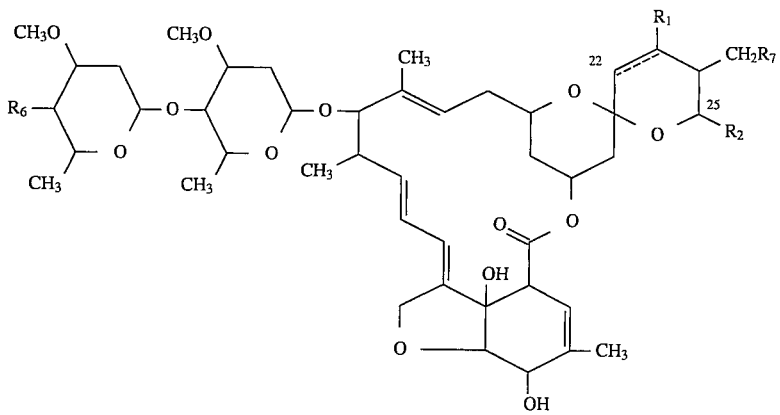

wherein the broken line represents a single bond; $R_1$ is hydrogen; $R_2$ is isopropyl of sec-butyl; $R_6$ is hydroxy, amino, mono-or di-$C_1$ to $C_6$ alkyl-amino or $C_1$ to $C_6$ alkanoylamino; and $R_7$ is hydrogen, hydroxy, or loweralkyl.

The term "loweralkyl" when used in the instant application is intended to represent those alkyl groups either straight or branched chain which have from 1–5 carbon atoms. Examples of such alkyl groups are methyl, ethyl, propyl, iso-propyl, butyl, sec-butyl, pentyl, and the like.

The term "loweralkanoyl" is intended to include those alkanoyl groups containing from one to five carbon atoms in either a straight or branched chain. Examples of such alkanoyl groups are formyl, acetyl, propenyl, butyryl, valeryl, and the like.

The term "halogen" is intended to include those halogen atoms fluorine, chlorine, bromine and iodine.

Examples of preferred compounds of the instant invention are:

4"-keto avermectin B1;
4"-keto avermectin B1;
4"-keto-22,23-dihydro avermectin B1;
4"-keto-22,23-dihydro avermectin B1;
4"-deoxy-4"-amino avermectin B1;
4"-deoxy-4"-amino avermectin B2;
4"-deoxy-4"-amino-22,23-dihydro avermectin B1;
4"-deoxy-4"-amino-22,23-dihydro avermectin B1;
4"-deoxy-4"-acetylamino avermectin B1;
4"-deoxy-4"-acetylamino avermectin B2;
4"-deoxy-4"-acetylamino-22,23-dihydro avermectin B1;
4"-deoxy-4"-acetylamino-22,23-dihydro avermectin B1;
4"-deoxy-4"-dimethylamino avermectin B1;
4"-deoxy-4"-dimethylamino avermectin B1;
4"-deoxy-4"-dimethylamino-22,23-dihydro avermectin B1;
4"-deoxy-4"-dimethylamino-22,23-dihydro avermectin B1;
4"-deoxy-4"-p-chloro benzenesulfonylamino-22,23-dihydro avermectin B1;
4"-deoxy-4"-p-chloro benzenesulfonylamino-22,23-dihydro avermectin B1;
4"-deoxy-4"-(2-methylbenzenesulfonylamino)-avermectin B1;
4"-deoxy-4"-(2-methylbenzenesulfonylamino)-avermectin B1.

The "b" compounds, those with a 25-iso-propyl group, are not necessarily separated from the corresponding "a" compound with a 25-sec-butyl group and the compounds are generally isolated as mixtures of the two compounds, consisting of at least 80% of the sec-butyl compound and no more than 20% of the iso-propyl compound. Thus, references in the instant application to "a" compounds such as B1a, A1a, and the like, are construed to actually contain a certain proportion of the corresponding "b" compound. Alternatively, this representation of a mixture is sometimes done by referring to the B1 or B2 compounds or by separating the "a" compound from the "b" compound by a slash (/) such as B1a/B1b, B2a/B2b and the like. Additionally, the products of synthetic procedures such as racemization or epimerization, procedures known to those skilled in the art, can be a mixture of stereoisomers. In particular, the stereoisomers at the 13- and 23-positions may be oriented either α- or β- representing such groups being below or above the general plane of the molecule, respectively. In each case, and at other positions in the molecule, both the α- and β-configurations are intended to be included within the ambit of this invention.

A related family of natural products also useful in the present invention is known as the milbemycins. The milbemycins have the same macrocyclic ring structures as the avermectins but have no substitution at position 13 ($R_4$= hydrogen) and have a methyl or ethyl group at position 25 ($R_2$=methyl or ethyl rather than isopropyl or sec-butyl as in the avermectins). The milbemycins and the fermentation conditions used to prepare them are described in U.S. Pat. No. 3,950,360. Closely related 13-deoxyavermectin aglycones are prepared by chemical modification of the natural avermectins and have been described in U.S. Pat. No. 4,173,571.

In the topical forms of the avermectin formulation it has not been possible to provide a formulation which provides an acceptable efficacy against ectoparasites, especially Chorioptes. Additionally, currently available topical formulations do not provide a zero milk withdrawal time with the application of endectocides which thus precludes the use of such compounds on milk producing animals.

The instant formulation of an avermectin compound with the above mentioned carriers gives the advantages of a readily pour-on topical formulation which provides the animal with effective treatment and protection against endoparasites and ectoparasites, especially Chorioptes and at the same time maintains the concentration of the active compound in the milk of dairy animals below a safe concentration for human consumption. Additional advantages of this invention are that the formulation is non-flammable, it is not readily washable by rain, it has good spreadability and cold temperature usage and has good compatibility with currently available dosing devices.

The avermectin formulation can contain the avermectin compound and the glycol or glyceride carrier as the only ingredients. The formulations will generally be prepared to administer a safe and effective amount from about 0.005 to about 10% by weight of the avermectin component, most preferrably from about 0.01 to about 5% by weight. Most preferably a formulation containing about 0.5% of the avermectin is employed. At a preferred dose volume of about 5 ml to treat 50 kg of animal body weight, the formulation contains from about 1.0 to about 50 mg of avermectin compound per ml of solution. The glycol or glyceride carrier is added to the formulation from about 40 to about 100% (q.s.v/v).

The most preferred formulation contains in addition to the glycol or glyceride carriers and avermectin compound, an antioxidant such as propyl gallate, BHA (butylated hydroxy anisole), BHT (butylated hydroxy toluene) monothioglycerol and the like, preferably BHT. The anti-oxidants are generally added to the formulation at rates of from about 0.005 to about 1.0% (w/v). Additives such as Crodamol CAP, glycerol formal, Tween 80 propylene glycol and the like, preferably Crodamol CAP, may also be used. The additives are generally added to the formulation at volumes of up to about 60% of the volume of glycol or glyceride carrier, preferably up to about 40% of the volume of carrier.

The formulation is prepared by dissolving the avermectin compound in approximately 50–100% of the intended volume of the above mentioned carriers and then adjusting the volume to 100% by the addition of the final volume of the carrier or additive. The anti-oxidant and additive may be combined with the above mentioned carriers prior to mixing the avermectin or added as the final volume of solvent.

The avermectin topical pour-on formulation may be administered to warm blooded animals to provide long acting treatment and protection against endoparasites and ectoparasites. Typically the formulation is administered to domesticated animals such as cattle, sheep, pigs, horses and the like.

The following example is provided in order that the invention might be more fully understood. It is not to be construed as a limitation of the invention.

EXAMPLE OF THE INVENTION

The formulations of this invention depend upon the particular avermectin compound and treatment. The avermectin is dissolved in approximately 50% of the glycol or glyceride carrier. When dissolved, the antioxidant and/or additive are optionally added and the volume adjusted to 100% with the final volume of glycol or glyceride carrier. The solution is mixed until it becomes homogeneous. Generally, mixing at room temperature (15°–25° C.) is adequate however, if necessary, warming up to 50° C. may be helpful. The following are nonlimiting examples of the composition of the present invention, which are conventionally formulated by mixing all components as stated above.

| Composition I | |
|---|---|
| 4"-acetylamino-4"-deoxyavermectin B1 | 0.5% w/v |
| BHT | 0.01% w/v |
| Crodamol CAP | 10.0% v/v |
| Miglyol 840 (q.s.) | 100.0% v/v |

| Composition II | |
|---|---|
| 4"-acetylamino-4"-deoxyavermectin B1 | 0.5% w/v |
| BHT | 0.01% w/v |
| Miglyol 840 (q.s.) | 100.0% v/v |

| Composition III | |
|---|---|
| 4"-acetylamino-4"-deoxyavermectin B1 | 0.5% w/v |
| BHT | 0.01% w/v |
| Isopropyl Myristate | 10.0% v/v |
| Miglyol 840 (q.s.) | 100.0% v/v |

| Composition IV | |
|---|---|
| 4"-acetylamino-4"-deoxyavermectin B1 | 0.5% w/v |
| Triacetin | 50.0% v/v |
| Miglyol 840 (q.s.) | 100.0% v/v |

| Composition V | |
|---|---|
| 4"-acetylamino-4"-deoxyavermectin B1 | 0.5% w/v |
| Softigen 767 | 65.0% v/v |
| Miglyol 840 | 25.0% v/v |
| Ethanol (q.s.) | 100.0% v/v |

| Composition VI | |
|---|---|
| 4"-acetylamino-4"-deoxyavermectin | 0.5% w/v |
| Softigen 767 | 65.0% v/v |
| Isopropanol (q.s.) | 100.0% v/v |

| Composition VII | |
|---|---|
| 4"-acetylamino-4"-deoxyavermectin B1 | 0.5% w/v |
| BHT | 0.01% w/v |
| Dowanol DB (q.s.) | 100.00% v/v |

Crodamol CAP is a tradename mixture of isopropyl myristate, cetyl octanoate and stearyl octanoate and Dowanol DB is a tradename for diethylene glycol butyl ether.

EXAMPLE II

The data below are results indicating the avermectin concentration (ng/ml) in the milk of lactating cows after topical application with some of the above formulations and that the avermectin concentration is maintained below 48 ng/ml which is the milk concentration of avermectin required for a zero milk withdrawal.

4'-ACETYLAMINO-4"-DEOXYAVERMECTIN B1
CONCENTRATIONS (ng/mL) IN MILK
OF LACTATING COWS DOSED TOPICALLY

| ANIMAL # | DAY POST DOSE | | | | | | | |
|---|---|---|---|---|---|---|---|---|
| | 0 | 1 | 2 | 3 | 4 | 5 | 6 | 7 |
| TREATMENT A: MIGLYOL 840/BHT/500 ug/kg | | | | | | | | |
| 5950 | 0.0 | 1.5 | 5.0 | 6.4 | 9.5 | 8.7 | 8.1 | 6.3 |
| 5931 | 0.0 | 6.0 | 23.2 | 13.0 | 7.1 | 4.2 | 2.5 | 1.7 |
| 5932 | 0.0 | 3.4 | 4.8 | 3.4 | 3.1 | 2.0 | 1.6 | 3.4 |
| 5938 | 0.0 | 5.6 | 15.5 | 9.6 | 8.5 | 4.5 | 3.7 | 3.1 |
| MEAN | 0.0 | 4.1 | 12.1 | 8.1 | 7.1 | 4.9 | 4.0 | 3.6 |
| STD. DEV. | | 2.1 | 8.9 | 4.1 | 2.8 | 2.8 | 2.9 | 1.9 |
| TREATMENT B: TRIACETIN/MIGLYOL 840 (50/50)/500 ug/kg | | | | | | | | |
| 5946 | 0.0 | 1.2 | 2.9 | 4.0 | 5.0 | 4.7 | 4.1 | 2.9 |
| 5949 | 0.0 | 2.7 | 13.3 | 11.4 | 8.6 | 5.3 | 3.5 | 2.8 |
| 5929 | 0.0 | 1.3 | 2.8 | 4.1 | 5.8 | 5.7 | 4.2 | 3.0 |
| 5928 | 0.0 | 4.9 | 14.6 | 9.4 | 5.4 | 3.1 | 2.0 | 1.4 |
| MEAN | 0.0 | 2.5 | 8.4 | 7.2 | 6.2 | 4.7 | 3.5 | 2.5 |
| STD DEV. | | 1.7 | 6.4 | 3.8 | 1.6 | 1.1 | 1.0 | 0.8 |
| TREATMENT C: SOFTIGEN 767/MIGLYOL 840 (70/30)/ 500 ug/kg | | | | | | | | |
| 5948 | 0.0 | 1.1 | 4.5 | 6.4 | 6.6 | 7.1 | 5.4 | 3.8 |
| 5930 | 0.0 | 1.4 | 3.8 | 3.9 | 5.8 | 9.0 | 7.6 | 4.9 |

4'-ACETYLAMINO-4"-DEOXYAVERMECTIN B1 CONCENTRATIONS (ng/mL) IN MILK OF LACTATING COWS DOSED TOPICALLY

| ANIMAL # | DAY POST DOSE | | | | | | | |
|---|---|---|---|---|---|---|---|---|
| | 0 | 1 | 2 | 3 | 4 | 5 | 6 | 7 |
| 5927 | 0.0 | 2.7 | 6.0 | 7.0 | 7.6 | 5.5 | 4.6 | 3.7 |
| 5934 | 0.0 | 1.9 | 4.7 | 10.6 | 15.0 | 8.3 | 4.9 | 3.2 |
| MEAN | 0.0 | 1.8 | 4.8 | 7.0 | 8.8 | 7.5 | 5.6 | 3.9 |
| STD. DEV. | | 0.7 | 0.9 | 3.9 | 4.2 | 1.5 | 1.4 | 0.7 |

TREATMENT D: Miglyol/Crodamol CAP (90/10)-500 µg/Kg

| | 0 | 1 | 2 | 3 | 4 | 5 | 6 | 7 |
|---|---|---|---|---|---|---|---|---|
| 6384 | 0.0 | 2.1 | 4.8 | 6.8 | 7.6 | 5.7 | 5.4 | 3.8 |
| 6385 | 0.0 | 7.3 | 7.1 | 6.1 | 4.8 | 3.3 | 2.7 | 2.3 |
| 6379 | 0.0 | 10.0 | 10.6 | 7.8 | 5.4 | 2.9 | 1.9 | 1.7 |
| 6386 | 0.0 | 2.7 | 6.0 | 6.0 | 5.8 | 4.1 | 5.4 | 5.2 |
| 6377 | 0.0 | 5.2 | 9.7 | 8.7 | 9.8 | 4.8 | 2.9 | 2.5 |
| 6382 | 0.0 | 7.7 | 15.5 | 11.8 | 8.7 | 4.7 | 3.3 | 2.3 |
| MEAN | 0.0 | 5.8 | 9.0 | 7.9 | 7.0 | 4.3 | 3.6 | 3.0 |
| STD. DEV. | | 3.1 | 3.9 | 2.2 | 2.0 | 1.0 | 1.5 | 1.3 |

TREATMENT E: Miglyol/Crodamol CAP (90/10)-250 µg/Kg

| | 0 | 1 | 2 | 3 | 4 | 5 | 6 | 7 |
|---|---|---|---|---|---|---|---|---|
| 6389 | 0.0 | 1.2 | 2.7 | 2.8 | 2.6 | 1.9 | 1.7 | 1.4 |
| 6381 | 0.0 | 1.0 | 1.6 | 1.8 | 2.8 | 2.5 | 2.6 | 2.0 |
| 6380 | 0.0 | 2.8 | 5.5 | 4.4 | 3.5 | 2.0 | 1.5 | 0.0 |
| 6378 | 0.0 | 2.4 | 4.8 | 4.0 | 2.9 | 1.6 | 1.1 | 0.0 |
| 6376 | 0.0 | 1.8 | 4.2 | 4.3 | 4.3 | 3.1 | 2.4 | 1.9 |
| 6388 | 0.0 | 0.0 | 1.3 | 1.7 | 2.8 | 2.3 | 2.0 | 1.9 |
| MEAN | 0.0 | 1.5 | 3.4 | 3.2 | 3.2 | 2.2 | 1.9 | 1.2 |
| STD. DEV. | | 1.0 | 1.7 | 1.2 | 0.6 | 0.5 | 0.6 | 1.0 |

TREATMENT F: TRIACETIN/MIGLYOL 840 (50/50)/500 ug/kg

| | 0 | 1 | 2 | 3 | 4 | 5 | 6 | 7 |
|---|---|---|---|---|---|---|---|---|
| 5977 | 0.0 | 1.4 | 6.8 | 6.9 | 4.3 | 3.4 | 3.0 | 2.2 |
| 5976 | 0.0 | 2.1 | 10.8 | 13.8 | 5.7 | 5.6 | 2.9 | 1.8 |
| MEAN | 0.0 | 1.8 | 8.8 | 10.4 | 5.0 | 4.5 | 3.0 | 2.0 |
| STD. DEV. | | 0.5 | 2.8 | 4.9 | 1.0 | 1.6 | 0.0 | 0.3 |

TREATMENT: G IPA/SOFTGEN 767 (40/60)/500 ug/kg

| | 0 | 1 | 2 | 3 | 4 | 5 | 6 | 7 |
|---|---|---|---|---|---|---|---|---|
| 5984 | 0.0 | 0.0 | 0.0 | 0.6 | 0.6 | 0.7 | 1.0 | 1.6 |
| 5980 | 0.0 | 0.5 | 0.8 | 1.6 | 1.3 | 2.9 | 2.3 | 2.8 |
| 5987 | 0.0 | 0.0 | 0.5 | 0.9 | 3.1 | 6.3 | 4.6 | 5.0 |
| 5982 | 0.0 | 0.0 | 2.0 | 3.8 | 3.8 | 3.5 | 2.2 | 1.6 |
| MEAN | 0.0 | 0.0 | 0.8 | 1.7 | 2.2 | 3.4 | 2.5 | 2.8 |
| STD. DEV. | | 0.0 | 0.9 | 1.5 | 1.5 | 2.3 | 1.5 | 1.6 |

NOTE:
Samples with 4"-acetylamino-4"-deoxyavermectin B1 concentrations equal to or less than 0.4 ng/ml are reported as 0 ng/ml:

EXAMPLE III

Efficacy trials with Chorioptes and key endoparasites were conducted to evaluate some of the above formulations. For each trial evaluating Chorioptes, four cattle were infested with *Chorioptes bovis* on Day -1 and treatment was given on Day 0. Respecting the trials evaluating endoparasites, the animals were challenged with Oesophagostamum, Trichuris and Dictyocaulus 17, 7, and 7 days before treatment with the formulation. The results are below.

CHORIOPTES MITE COUNTS

| An. No. | Day -1 | Day 7 | Day 14 | Day 21 | Day 27 | Day 35 |
|---|---|---|---|---|---|---|
| Trt. 1 - Untreated Control | | | | | | |
| H215 | 32 | 3 | 0 | 10 | 0 | 0 |
| H208 | 6 | 19 | 15 | 3 | 4 | 17 |
| H229 | 708 | 5024 | 2546 | 601[a] | 11477[b] | 6835 |
| H233 | 511 | 875 | 1430 | 889[a] | 1432[b] | 1339 |
| Trt. 2 - 4"-aa-4"deoxy in Miglyol 840/Crodamol CAP/BHT at 500 mcg/kg | | | | | | |
| H224 | 22 | 1 | 79 | 2 | 0 | 0 |
| H223 | 17 | 0 | 0 | 0 | 0 | 0 |
| H234 | 2018 | 1007 | 895 | 0[a] | 0[b] | 0 |
| H230 | 378 | 265 | 2 | 5[a] | 0[b] | 150 |
| Trt. 3 - 4"-aa-4"deoxy in Miglyol 840/BHT at 500 mcg/kg | | | | | | |
| H226 | 182 | 3 | 0 | 1 | 0 | 0 |
| H218 | 3 | 0 | 0 | 0 | 0 | 0 |
| H228 | 1644 | 659 | 16 | 0[a] | 0[b] | 0 |
| H231 | 233 | 358 | 603 | 133[a] | 89[b] | 5 |

[a] Day 20
[b] Day 28

L-653,648 Nematode Counts
Total Counts based on 10% aliquots
(Dictyocaulus counts are total counts)

| Animal Number | Oesophagost spp. Adult | Oesophagost spp L$_4$ | Trichuris spp. Adult | Dictyocaulus spp. |
|---|---|---|---|---|
| Trt. - Untreated Control | | | | |
| 2477 | 0 | 0 | 20 | 3 |
| 2374 | 50 | 0 | 0 | 0 |
| 2259 | 0 | 0 | 50 | 17 |
| 41 | 240 | 0 | 80 | 14 |
| Trt. 2 - 4"-aa-4"deoxy in Miglyol 840 Crodamol CAP/BHT (0.5%/q.s./10%/0.01% at 500 mcg/kg | | | | |
| 2456 | 0 | 0 | 0 | 0 |
| 2478 | 0 | 0 | 0 | 0 |
| 5 | 0 | 0 | 0 | 0 |
| 2254 | 0 | 0 | 0 | 0 |
| Trt. 3 - 4"-aa-4"deoxy in Miglyol 840 BHT (0.5%/q.s/0.01%) at 500 mcg/kg | | | | |
| 2510 | 0 | 0 | 0 | 0 |
| 2358 | 0 | 0 | 0 | 0 |
| 40 | 0 | 0 | 0 | 0 |
| 2258 | 0 | 0 | 0 | 0 |
| Trt. 4 - 4"-aa-4"deoxy in Miglyol 840/Lauroglycol/BHT (0.5%/q.s./10%/0.01%) at 500 mcg/kg | | | | |
| 2528 | 0 | 0 | 0 | 0 |
| 2443 | 0 | 0 | 0 | 0 |
| 44 | 0 | 0 | 0 | 0 |
| 2298 | 0 | 0 | 0 | 0 |

What is claimed is:

1. A topical pour-on formulation for the treatment of ecto and endoparasites, which provides a zero-milk withdrawal time in dairy animals, consisting of from about 40 to about 100% q.s., v/v of a glyceride or derivative thereof carrier selected from the group consisting of propylene dicaprylate/dicaprate, and caprylic/capric triglyceride, and from about 0.005 to about 10% w/v of an avermectin compound having the formula:

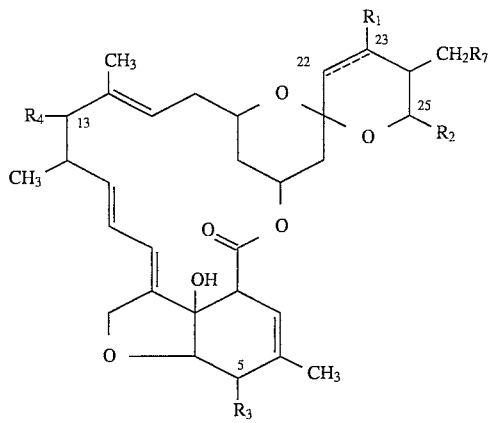

where the broken line indicates a single or a double bond at the 22, 23-positions;

$R_1$ is hydrogen or hydroxy, provided that $R_1$ is present only when the broken line indicates a single bond;

$R_2$ is alkyl of from 1 to 6 carbon atoms or alkenyl of from 3 to 6 carbon atoms or cycloalkyl of from 3 to 6 carbon atoms;

$R_3$ is hydroxy, methoxy, or =$NOR_5$; where $R_5$ is hydrogen or lower alkyl;

$R_7$ is hydrogen, hydroxy or lower alkyl; and $R_4$ is

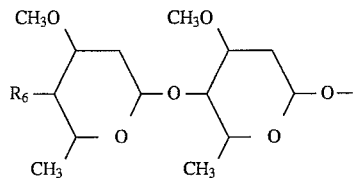

where $R_6$ is hydroxy, amino, mono- or di-$C_1$–$C_6$ alkylamino or $C_1$–$C_6$ alkanolylamino.

2. The formulation of claim 1 which contains from about 0.01 to about 5% w/v of the avermectin compound.

3. The formulation of claim 1 which contains in addition to the carrier and the avermectin compound, an anti-oxidant from about 0.005 to about 1.0% w/v.

4. The formulation of claim 3 wherein the antioxidant is selected from the group consisting of n-propyl fallate, BHA, BHT, or monothioglycerol.

5. The formulation of claim 4 wherein the antioxidant is BHT.

6. The formulation of claim 1 which optionally contains an additional solvent at up to about 60% v/v, the solvent being selected from the group consisting of Crodamol Cap, glycerol formal, Tween 80, or propylene glycol.

7. The formulation of claim 1 consisting of 100% q.s., v/v propylene dicaprylate/dicaprate or caprylate/caprate glyceride, from about 0.005 to about 0.05% w/v BHT and from about 0.01 to about 5% w/v of 4"-acetylamino-4"-deoxyavermectin B1.

8. The formulation of claim 7 consisting of about 0.5% w/v of 4"-acetylamino-4"-deoxyavermectin B1, and about 0.01% w/v BHT.

9. A method for the treatment of internal and external parasites of animals, which provides a zero-milk withdrawal time in dairy animals, which comprises topically applying an effective amount of a formulation consisting of from about 40 to about 100% q.s., v/v of a glyceride or derivative thereof carrier selected from the group consisting of propylene dicaprylate/dicaprate, and caprylic/capric triglyceride, and from about 0.005.to about 10% w/v of an avermectin compound having the formula:

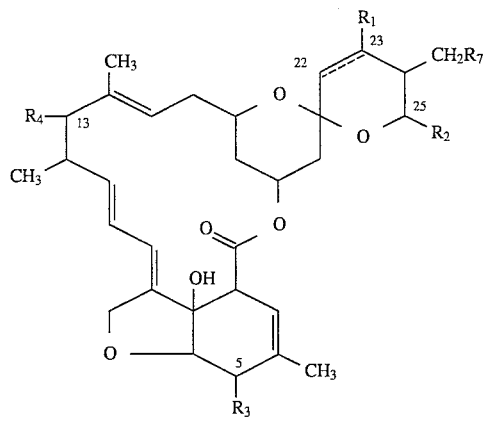

where the broken line indicates a single or a double bond at the 22, 23-positions;

$R_1$ is hydrogen or hydroxy, provided that $R_1$ is present only when the line indicates a single bond;

$R_2$ is alkyl of from 1 to 6 carbon atoms or alkenyl of from 3 to 6 carbon atoms or cycloalkyl of from 3to 6 carbon atoms;

$R_3$ is hydroxy, methoxy, or=$NOR_5$; where $R_5$ is hydrogen or lower alkyl;

$R_7$ is hydrogen, hydroxy or lower alkyl; and $R_4$ is

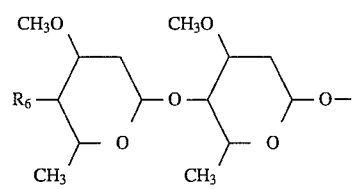

where $R_6$ is hydroxy, amino, mono- or di-$C_1$–$C_6$ alkylamino or $C_1$–$C_6$ alkanolylamino, to the skin of an animal.

* * * * *